United States Patent
Girouard et al.

(10) Patent No.: US 6,721,596 B1
(45) Date of Patent: Apr. 13, 2004

(54) ATRIAL SHOCK THERAPY WITH VENTRICULAR PACING

(75) Inventors: Steven D. Girouard, Woodbury, MN (US); Kirsten Rodenhiser, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/571,676

(22) Filed: May 15, 2000

(51) Int. Cl.$^7$ .................................................. A61N 1/36
(52) U.S. Cl. ............................................................. 607/4
(58) Field of Search ................................. 607/4, 14, 5

(56) References Cited

U.S. PATENT DOCUMENTS

| | | | |
|---|---|---|---|
| 4,554,922 A | 11/1985 | Prystowsky et al. ........ 128/419 |
| 5,207,219 A | * 5/1993 | Adams ........................... 607/5 |
| 5,282,836 A | * 2/1994 | Kreyenhagen et al. ......... 607/4 |
| 5,332,400 A | 7/1994 | Alferness ........................ 607/5 |
| 5,395,373 A | 3/1995 | Ayers ............................. 607/8 |
| 5,411,524 A | 5/1995 | Rahul ............................. 607/4 |
| 5,480,413 A | 1/1996 | Greenhut et al. ............. 607/14 |
| 5,554,174 A | 9/1996 | Causey, III ..................... 607/5 |
| 5,591,215 A | 1/1997 | Greenhut et al. ............. 607/14 |
| 5,674,250 A | 10/1997 | de Coriolis et al. ............ 607/7 |
| 5,776,164 A | 7/1998 | Ripart ............................. 607/5 |
| 5,840,079 A | 11/1998 | Warman et al. ................. 607/4 |
| 5,853,426 A | 12/1998 | Shieh .............................. 607/5 |
| 5,865,838 A | 2/1999 | Obel et al. ...................... 607/5 |
| 5,987,354 A | 11/1999 | Cooper et al. .................. 607/5 |
| 5,999,850 A | * 12/1999 | Dawson .......................... 607/4 |
| 6,047,210 A | 4/2000 | Kim et al. ....................... 607/4 |
| 6,085,116 A | 7/2000 | Pendekanti et al. ............ 607/5 |
| 6,430,438 B1 | * 8/2002 | Chen et al. ..................... 607/5 |

* cited by examiner

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

An apparatus and method for delivering electrical shock therapy in order to treat atrial tachyarrhythmias such as fibrillation is disclosed where pre-shock ventricular pacing is employed to modify the intrinsic ventricular rhythm during the tachyarrhythmic episode. By making the intrinsic ventricular rhythm slower and more predictable, an atrial defibrillation shock may be delivered with less risk of inducing ventricular fibrillation.

20 Claims, 1 Drawing Sheet

ATRIAL SHOCK THERAPY WITH VENTRICULAR PACING

FIELD OF THE INVENTION

This invention pertains to methods for treating atrial tachyarrhythmias. In particular, the invention relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and may also incorporate cardiac pacing functionality.

The most dangerous tachyarrhythmias are ventricular tachycardia and ventricular fibrillation, and ICDs have most commonly been applied in the treatment of those. conditions. ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrioventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As aforesaid, an ICD terminates atrial fibrillation by delivering a shock pulse to electrodes disposed in or near the atria. The resulting depolarization also spreads to the ventricles, however, and there is a risk that such an atrial shock pulse can actually induce ventricular fibrillation, a condition much worse than atrial fibrillation. To lessen this risk, current ICDs delay delivering an atrial shock pulse until the intrinsic ventricular rhythm is below a specified maximum rate and then deliver the shock synchronously with a sensed ventricular depolarization (i.e., an R wave). That is, an R—R interval, which is the time between a presently sensed R wave and the preceding R wave, is measured. If the R—R interval is above a specified minimum value, the interval is considered shockable and the atrial defibrillation shock pulse is delivered.

If the ventricular rhythm does not slow to a safe rate in a short time, however, the delay in delivering atrial defibrillation therapy may be deleterious to the patient. In addition, a particular subset of patients have spontaneous ventricular rhythms during atrial fibrillation that may remain too rapid to ever safely deliver an atrial defibrillation shock, and these patients may not be suitable candidates for ICD therapy for that reason. Furthermore, the ventricular rhythms that occur during an episode of atrial fibrillation are inherently rapid and irregular, and certain R—R interval sequences, such as a long-short R—R interval sequence are particularly dangerous for shock timing. Overcoming these problems is a primary objective of the present invention.

SUMMARY OF THE INVENTION

The present invention is a method and apparatus for delivering atrial defibrillation therapy in which delivery of an atrial defibrillation shock pulse is preceded by ventricular pacing in order to decrease the intrinsic ventricular rhythm to a rate at which the atrial defibrillation shock pulse can be more safely delivered. In accordance with the invention, after atrial fibrillation is detected, a sequence of one or more ventricular pacing pulses is delivered at a rate intended to be above the intrinsic ventricular rate. After the last pacing pulse in the sequence is delivered, a compensatory pause is produced before the next intrinsic ventricular beat. The atrial defibrillation shock pulse can then be delivered synchronously with that beat if the R—R interval is above a specified minimum value.

DETAILED DESCRIPTION OF THE INVENTION

Figure 1:
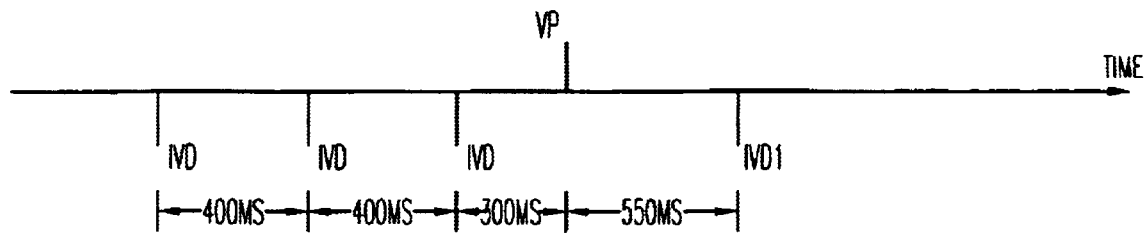
FIG. 1 is a system diagram of an implantable defibrillator.

The present invention is a method and apparatus for delivering atrial defibrillation shock therapy. As used herein, atrial defibrillation shock therapy should be taken to mean shock therapy for treating any atrial tachyarrhythmia, such as atrial flutter, as well as atrial fibrillation.

In order to avoid the possible induction of ventricular fibrillation, atrial defibrillation shocks should be delivered synchronously with a sensed R wave and after a minimum pre-shock R—R interval. (The R—R interval is the time between the immediately preceding R wave and the presently sensed R wave, and an R wave may be regarded as either a spontaneously occurring depolarization or a ventricular pace.) This is done because the ventricle is especially vulnerable to induction of fibrillation by a depolarizing shock delivered at a time too near the end of the preceding ventricular contraction (i.e., close to the T wave on an EKG). Delivering the shock synchronously with a sensed R wave thus moves the shock away from the vulnerable period, but at a very rapid ventricular rhythm, the ventricular beats may be so close together that even synchronously delivered shocks may induce ventricular fibrillation. Shocking should therefore be delayed until the ventricular rhythm is slow enough to safely deliver the defibrillation pulse as determined by measuring the R—R interval. As noted above, however, the intrinsic ventricular rhythm during atrial fibrillation tends to be both rapid and irregular. If the intrinsic rhythm could be slowed and made more predictable, an atrial defibrillation shock could be more safely delivered.

The intrinsic ventricular rhythm that occurs during an episode of atrial fibrillation is a result of the chaotically occurring depolarizations occurring in the atria being passed through the AV node to the ventricles. The intrinsic ventricular rate is thus governed by the cycle length of the atrial fibrillation and the refractory period of the AV node. If a ventricular pacing pulse is delivered before the next intrinsic beat occurs, the ventricular depolarization is conducted retrogradely to the AV node causing late depolarization of the AV node during the ventricular beat. The refractory period of the AV node is also delayed which delays the time before an atrial depolarization can be conducted through the node to result in an intrinsic beat. The effect of the pace is thus to lengthen the next R—R interval. The approach of the present invention is to overdrive the intrinsic ventricular rhythm during atrial fibrillation by pacing the ventricles at a rate greater than the intrinsic rate before delivering an atrial defibrillation pulse. The effect of such pacing is to make the intrinsic rhythm slower and more predictable, transiently increasing the probability of a shockable R—R interval occurring. Overdrive ventricular pacing also shortens the preceding QT interval as the cardiac action potential accommodates to the higher rate. The shorter QT interval also increases the safety margin of a defibrillation shock by increasing the time between the preceding T wave and the shock. Pre-shock overdrive pacing also may shorten the time after detection of an atrial arrhythmia until a shock pulse can be delivered. Finally, a shockable R—R interval may never spontaneously occur with some rhythms such as atrial flutter (characterized by a rapid and regular ventricular rate), and pre-shock pacing may then make safe delivery of an atrial defibrillation shock pulse possible where it would not be otherwise.

FIG. 1 is a graphic representation of the above-described procedure. An exemplary sequence of intrinsic ventricular depolarizations IVD occurring during an episode of atrial fibrillation is shown having R—R intervals of 400 milliseconds. A ventricular pace VP is then delivered with a pacing interval of 300 milliseconds as measured from the last R wave. The next intrinsic beat IVD1 that occurs after the last pacing pulse is shown as having a longer R—R interval of 550 milliseconds due to the compensatory pause produced by the pacing and which may typically be regarded as a shockable R—R interval. Although not every pace might result in a shockable R—R interval as depicted in the figure, such pre-shock pacing greatly increases the probability of a longer, and hence shockable, R—R interval occurring.

Figure 2:
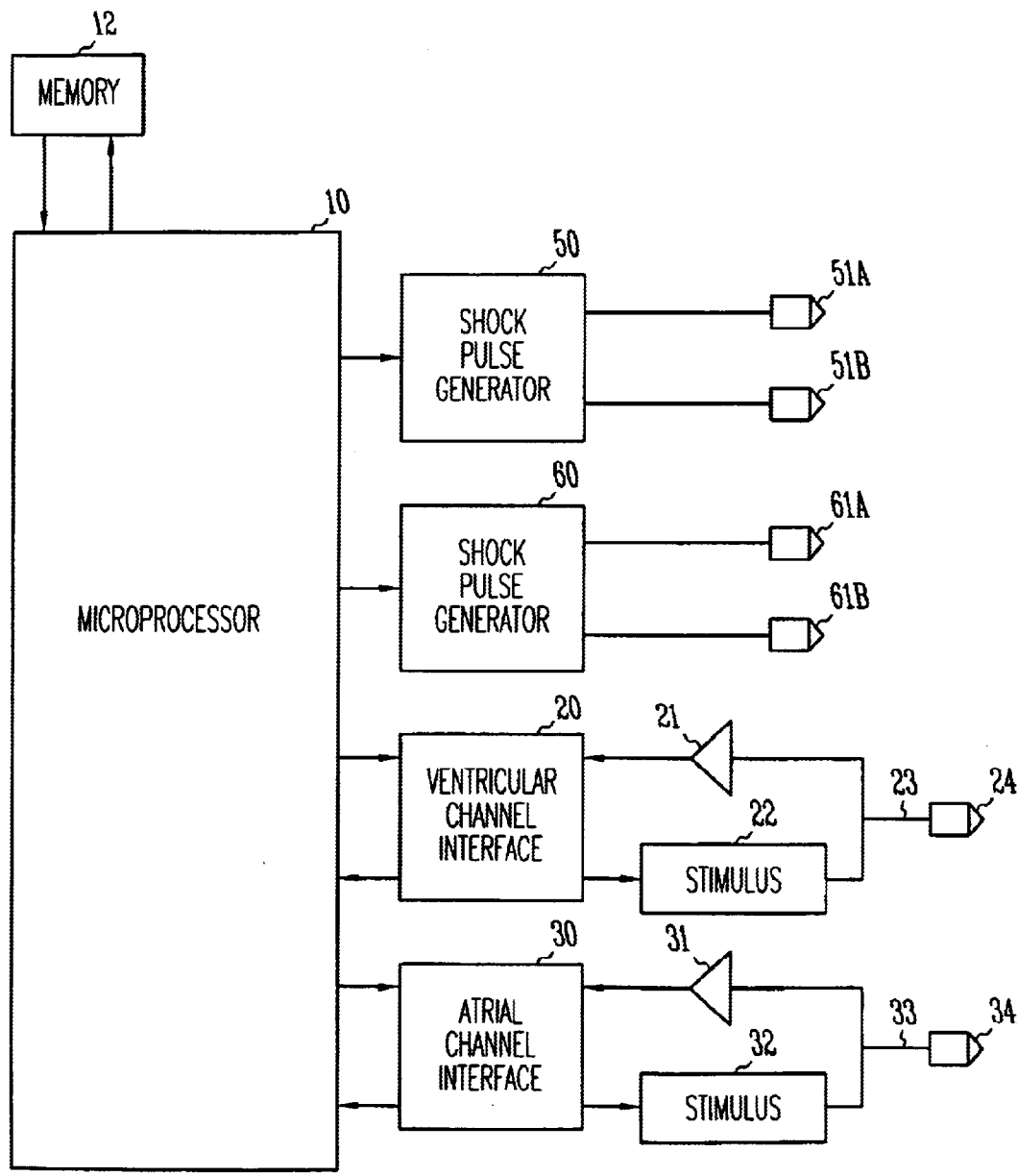
FIG. 2 is a timing diagram showing a sequence of pacing pulses and subsequent intrinsic beat.

FIG. 2 is a system diagram of a microprocessor-based implantable cardioverter/defibrillator device for treating atrial tachyarrthmias that also incorporates a pacemaker functionality. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used to control pacing and for measuring heart rate in order to detect tachyarrythmias such as fibrillation. The ICD detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. The defibrillation leads have along their length electrically conductive coils that act as electrodes for defibrillation stimuli. A similar shock pulse generator 60 and shock electrodes 61a and 61b are provided to deliver ventricular fibrillation therapy in the event of an induced ventricular fibrillation from atrial shock pulses.

The device depicted in FIG. 2 can be configured to deliver atrial defibrillation therapy in accordance with the invention as described above by appropriate programming of the microprocessor. Thus, once an episode of atrial fibrillation is detected with the atrial sensing channel, the device prepares to deliver an atrial defibrillation shock. The ventricular rhythm is monitored by measuring the R—R interval associated with each sensed R wave. If a sensed R wave occurs at an R—R interval longer than a specified minimum limit value, the interval is considered shockable so that the sensed R wave is safe to shock on. An atrial defibrillation shock is then delivered immediately so as to be practically synchronous with the sensed R wave. The device may wait for a programmable number (i.e., one or more) of sensed R waves for one to shock on before starting to pace the ventricle. If no shockable R—R interval occurs during those beats, a ventricular pace is delivered in an attempt to induce a compensatory pause that will result in the next R wave occurring at a shockable R—R interval. The ventricular pace may either be delivered at a specified pacing interval (i.e., the time from the preceding R wave to the pace) or at a pacing interval calculated as some function of the preceding measured R—R intervals. For example, the pacing interval could be calculated to be a specified amount shorter than the average of a number of preceding R—R intervals. In either case, the ventricular pace should be delivered at a pacing interval shorter than that of the spontaneous ventricular rhythm in order to induce the compensatory pause but not short enough to risk pacing during the vulnerable period. Also, once the decision is made to deliver a ventricular pace, a sensed R wave occurring before the pace should restart the pacing interval from that R wave. After a pace is delivered, an atrial defibrillation pulse is delivered synchronously with the next sensed R wave if the R—R interval is shockable. If the R—R interval is shorter than the minimum limit value, the device may either continue to wait for a shockable interval for a specified number of beats or for a specified length of time, or may deliver another pace in another attempt to slow the intrinsic rhythm.

The ventricular pacing can be delivered to the right, left, or both ventricles. Also, rather than delivering a single ventricular pace to induce the compensatory pause, the device may alternatively deliver a sequence of multiple pacing pulses in order to better ensure capture of the ventricle by the pacing. After a specified number of pacing pulses, the R wave occurring after the last pace is sensed, and an atrial defibrillation shock is delivered if the R—R interval is shockable. The pacing rate and number of pulses in the sequence can either be fixed at selected values or calculated dynamically as functions of the preceding R—R intervals. The device may also be programmed to deliver one or more pacing pulses at a different specified pacing intervals from other pacing pulses in the sequence. Another alternative is for the device to deliver a series of test pacing pulses to determine a transient pacing rate that will yield sufficiently long post-pacing R—R intervals.

It has also been found that delivering an atrial defibrillation shock on pre-shock R—R intervals that are excessively long can increase the incidence of early recurrence of atrial fibrillation (ERAF). In order to decrease the risk of this occurring, a maximum R—R interval limit value can also be specified. A shockable R—R interval then becomes one that falls within a window as defined by specified maximum and minimum limit values. An exemplary window might be an R—R interval between 500 and 800 milliseconds. In such a modified embodiment of the invention, ventricular pacing is initiated after detection of atrial fibrillation as before in order to produce a compensatory pause in the intrinsic ventricular rhythm. After the last pace in the sequence, the next R wave is sensed and the R—R interval is measured. If the interval is above the minimum limit value and below the maximum limit value so as to fall within the shockable window, an atrial defibrillation shock is delivered synchronously with the sensed R wave. If the R—R interval is below the limit value, the device may either wait for a shockable interval or deliver another pace (or sequence of paces). If no sensed R wave occurs before the maximum limit value of the R—R interval, on the other hand, the device may either wait and test the next R—R interval for shockability, or may deliver an atrial defibrillation shock pulse synchronously with another ventricular pace.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for delivering atrial defibrillation therapy, comprising:

detecting an episode of atrial fibrillation;

sensing ventricular depolarizations (R waves) and measuring an R—R interval for each sensed R wave;

delivering an atrial defibrillation shock pulse synchronously with a sensed R wave if a shockable R—R interval is measured, where a shockable R—R interval is defined as an interval longer than a specified minimum limit value; and, delivering a ventricular pace after the sensed R wave and before the next R wave if the R—R interval is below the specified minimum limit value.

2. The method of claim 1 further comprising delivering the ventricular pace at a specified pacing interval after a preceding R wave, wherein the pacing interval is selected to be below the specified minimum limit value of the R—R interval.

3. The method of claim 1 further comprising delivering the ventricular pace at a pacing interval calculated as a function of preceding measured R—R intervals.

4. The method of claim 1 further comprising delivering a sequence of multiple ventricular paces at a specified pacing interval if the R—R interval is below the specified minimum limit value in an attempt to lengthen the subsequent R—R interval.

5. The method of claim 4 further comprising delivering the sequence of multiple ventricular paces with the number of paces in the sequence and the pacing interval calculated as functions of preceding measured R—R intervals.

6. The method of claim 1 further comprising sensing a specified number of R waves in order to detect a shockable R—R interval before ventricular pacing is initiated.

7. The method of claim 1 wherein a shockable R—R interval is further defined as being below a specified maximum limit value.

8. The method of claim 7 further comprising delivering no atrial defibrillation shock if a measured R—R interval is below the specified maximum limit value.

9. The method of claim 7 delivering an atrial defibrillation shock synchronously with a ventricular pace if no R wave is sensed before the maximum limit value of the R—R interval.

10. The method of claim 7 wherein a shockable R—R interval is defined by minimum and maximum values of approximately 500 and 800 milliseconds, respectively.

11. An apparatus for delivering atrial defibrillation therapy, comprising:

an atrial sensing channel;

a ventricular sensing and pacing channel for sensing R waves and delivering ventricular paces;

a shock pulse generator for generating atrial defibrillation shock pulses;

a controller programmed to detect atrial fibrillation from data received from the atrial sensing channel;

wherein the controller is further programmed to control the operation of the shock pulse generator and ventricular pacing channel and to measure R—R intervals with each sensed R wave; and, wherein, after detecting an episode of atrial fibrillation, the controller is programmed to deliver an atrial defibrillation shock pulse synchronously with a sensed R wave if a shockable R—R interval is measured, wherein a shockable R—R interval is defined as an interval longer than a specified minimum limit value, and deliver a ventricular pace after the sensed R wave and before the next R wave if the R—R interval is below the specified minimum limit value.

12. The apparatus of claim 11 wherein the controller is programmed to deliver a ventricular pace at a specified pacing interval after a preceding R wave, wherein the pacing interval is selected to be below the specified minimum limit value of the R—R interval.

13. The apparatus of claim 11 wherein the controller is programmed to deliver a ventricular pace at a pacing interval calculated as a function of preceding measured R—R intervals.

14. The apparatus of claim 11 wherein the controller is programmed to deliver a sequence of multiple ventricular paces at a specified pacing interval if the R—R interval is below the specified minimum limit value.

15. The apparatus of claim 14 wherein the number of ventricular paces delivered and the pacing interval are calculated by the controller as functions of preceding measured R—R intervals.

16. The apparatus of claim 11 wherein the controller is programmed to sense a specified number of R waves in order to detect a shockable R—R interval before ventricular pacing is initiated.

17. The apparatus of claim 11 wherein a shockable R—R interval is further defined as being below a specified maximum limit value.

18. The apparatus of claim 17 wherein the controller is programmed to deliver an atrial defibrillation shock if a measured R—R interval is below the specified maximum limit value.

19. The apparatus of claim 17 wherein the controller is programmed to deliver an atrial defibrillation shock synchronously with a ventricular pace if no R wave is sensed before the maximum limit value of the R—R interval.

20. The apparatus of claim 17 wherein a shockable R—R interval is defined by minimum and maximum values of approximately 500 and 800 milliseconds, respectively.

* * * * *

UNITED STATES PATENT AND TRADEMARK OFFICE
CERTIFICATE OF CORRECTION

PATENT NO. : 6,721,596 B1
DATED : April 13, 2004
INVENTOR(S) : Girouard et al.

It is certified that error appears in the above-identified patent and that said Letters Patent is hereby corrected as shown below:

Title page,
Item [56], References Cited, U.S. PATENT DOCUMENTS, delete "*" and after "Adams" insert -- et al. --; and after "Dawson" insert -- et al. --.

Column 2,
Line 40, delete "FIG. 1 is a system diagram of an implantable defibrillator." and insert -- Fig. 1 is a timing diagram showing a sequence of pacing pulses and subsequent intrinsic beat. --, therefor.
Line 41, delete "FIG. 2 is a timing diagram showing a sequence of pacing pulses and subsequent intrinsic beat." and insert -- Fig. 2 is a system diagram of an implantable defibrillator. --, therefor.

Column 5,
Line 51, after "value;" delete "and,".
Line 54, delete "value." and insert -- value; and, measuring the R-R interval for the next R wave and delivering an atrial defibrillation shock pulse synchronously with the next R wave if the R-R interval is shockable. --, therefor.
Line 56, after "interval" delete "after a preceding R wave, wherein the pacing interval is".
Line 64, delete "sequence of multiple ventricular paces at a specified pacing interval if the R-R interval is below the specified minimum limit value in an attempt to lengthen the subsequent R-R interval." and insert -- second ventricular pace after the next R wave if the R-R interval for that R wave was not shockable and delivered no atrial defibrillation shock was, and delivering an atrial defibrillation shock pulse in synchrony with the R wave subsequent to that next R wave if the R-R interval is shockable. --, therefor.

Column 6,
Line 1, delete "claim 4" and insert -- claim 1 --, therefor.
Line 2, delete "the" (before "sequence") and insert -- a --, therefor.
Line 41, after "to" insert -- : --.
Line 44, delete "wherein" and insert -- where --, therefor.
Lines 45-46, delete ", and" and insert -- ; --, therefor.

UNITED STATES PATENT AND TRADEMARK OFFICE
CERTIFICATE OF CORRECTION

PATENT NO.    : 6,721,596 B1
DATED         : April 13, 2004
INVENTOR(S)   : Girouard et al.

It is certified that error appears in the above-identified patent and that said Letters Patent is hereby corrected as shown below:

Column 6, cont'd.,
Line 49, delete "value." and insert -- value; and, measure the R-R interval for the next R wave and deliver an atrial defibrillation shock pulse synchronously with the next R wave if the R-R interval is shockable. --, therefor.
Line 61, after "a" delete "sequence of multiple ventricular paces at a specified pacing interval if the R-R interval is below the specified minimum limit value." and insert -- second ventricular pace after the next R wave if the R-R interval for that R wave was not shockable and no atrial defibrillation shock was delivered, and deliver an atrial defibrillation shock pulse in synchrony with the R wave subsequent to that next R wave if the R-R interval is shockable. --, therefor.
Line 64, in after "wherein the" delete "number of ventricular paces delivered and the pacing interval are calculated by the controller as functions of preceding measured R-R intervals." and insert -- controller is programmed to deliver a sequence of multiple ventricular paces with the number of paces in the sequence and the pacing interval calculated as functions of preceding measured R-R intervals. --, therefor.

Signed and Sealed this

Thirteenth Day of July, 2004

JON W. DUDAS
*Acting Director of the United States Patent and Trademark Office*